United States Patent [19]

Dragan et al.

[11] Patent Number: 5,085,249
[45] Date of Patent: Feb. 4, 1992

[54] VALVE FOR A VASCULAR DILATING DEVICE

[75] Inventors: William B. Dragan, Easton; John J. Discko, Jr., Hamden, both of Conn.

[73] Assignee: Centrix, Inc., Milford, Conn.

[21] Appl. No.: 531,575

[22] Filed: Jun. 1, 1990

[51] Int. Cl.$^5$ .............................................. F16K 11/02
[52] U.S. Cl. ................................. 137/879; 137/625.33
[58] Field of Search .................................. 604/97–100; 137/625.33, 879, 881, 599.2, 512.1

Primary Examiner—John C. Fox
Attorney, Agent, or Firm—Paul A. Fattibene; Arthur T. Fattibene

[57] ABSTRACT

An improved valve for use in angioplasty comprising a cup shaped body having a piston adapted to slide into a first and second position therein. A passage and a plurality of chambers and openings are formed within the piston. The piston is biased in a first position to align openings and a passage for fluid to flow through a chamber and a one-way valve to inflate a balloon catheter. When the piston is forced into a second position, openings are aligned to permit fluid to flow from the balloon catheter into a chamber through a second one-way valve to rapidly deflat the balloon catheter. A balloon catheter can thereby be quickly deflated easily by a physician.

6 Claims, 2 Drawing Sheets

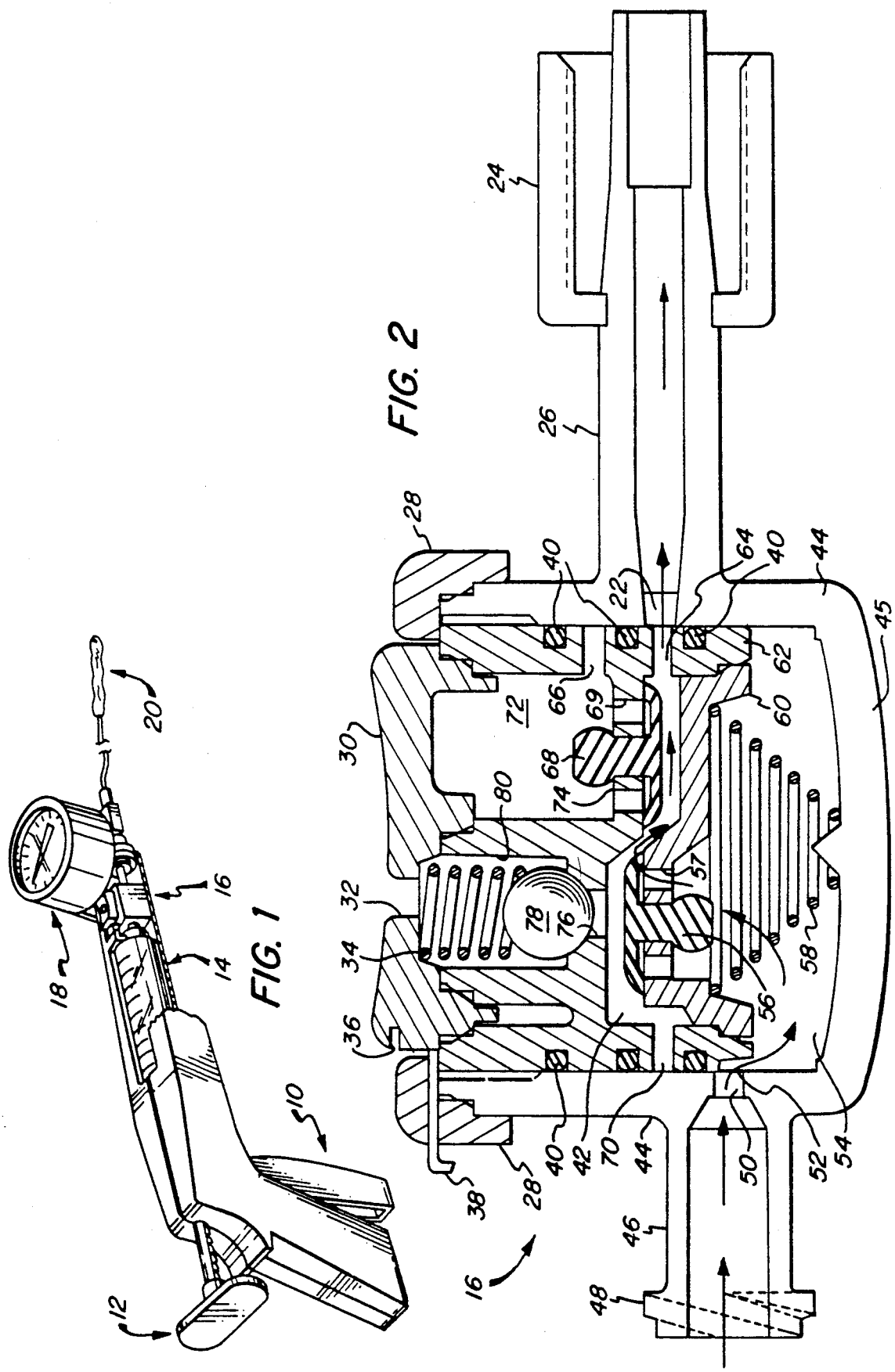

VALVE FOR A VASCULAR DILATING DEVICE

FIELD OF THE INVENTION

The present invention relates generally to a vascular dilating device for use in a coronary angioplasty procedure and more specifically to an improved valve for use therein.

BACKGROUND OF THE INVENTION

Angioplasty is a relatively recent technique for the treatment of cardiovascular disease caused by atherosclerosis. The original technique originally used progressively larger catheters to open a blocked artery. Later, a technique using a miniature balloon catheter was developed.

Since angioplasty is the treatment of choice in many cases of cardiovascular disease, there have been many attempts to improve the technique. When inserting the balloon catheter into the artery in an attempt to open the artery, high pressures often need to be developed. Many devices have been developed to generate these high pressures in a convenient device. One such device is illustrated in U.S. Pat. No. 4,654,027 issued Mar. 31, 1987 to Dragan et al, which is herein incorporated by reference. With the device disclosed in this patent, high pressures can quickly be obtained inflating the balloon catheter. This increases the likelihood of opening up the restricted or blocked artery.

However, due to the high pressures obtained, the balloon catheter could possibly come very close to rupturing the artery. When the pressure exceeds a predetermined value or behaves erratically, it is extremely critical to quickly deflate the balloon catheter to avoid possibly rupturing the artery being worked upon.

In many prior art devices, the balloon catheter could not be deflated as quickly as desired. A lever would typically have to be rotated 90 degrees to release the pressure within the balloon catheter. Often, the doctor would have to remove one hand from the device to rotate the lever when the balloon catheter needed to be deflated. Many times this occurred at a very critical moment when confusion or a slight delay could result in a rupturing of the artery. Rupturing of the artery could possibly be fatal to the patient.

Therefore, there is a need for a device that will permit quick and easy deflation of a balloon catheter used in angioplasty.

SUMMARY OF THE INVENTION

The present invention is directed to an improved valve to quickly release the pressure in a device used in angioplasty. A cup shaped body has an aperture at either side thereof. A piston having a plurality of chambers therein is positioned to slide within the cup shaped body in a first and second position. A passage extends through the piston permitting fluid flow therein. The piston is normally biased upward into a first position by a spring. In this first position, fluid can flow into an inlet chamber and through a one way valve into the passage to exit through the other side of the cup shaped body. The piston can be pushed downward into a second position. This seals the inlet chamber and opens the balloon side aperture to a pressure release chamber. From the pressure release chamber, the fluid can flow through a one-way valve to exit through an aperture.

Accordingly, it is an object of the present invention to quickly deflate a balloon catheter as used in angioplasty.

It is another object of the present invention to provide a valve that is easy to use.

It is an advantage of the present invention that it is easy to manufacture.

It is another advantage of the present invention that the pressure in a balloon catheter can be released without the doctor having to move his hand or release the device used in the angioplasty procedure.

It is yet another advantage of the present invention that in one embodiment a hold down latch is provided.

It is a feature of the present invention that multiple chambers are used.

It is another feature of the present invention that the piston can be positioned in a first inflating position and a second deflating position.

It is yet another feature of the present invention that a safety limit relief valve is provided to prevent rupture of the balloon catheter.

These and other objects, advantages, and features will become more readily apparent in view of the following more detailed description.

BRIEF DESCRIPTION OF THE DRAWINGS

FIG. 1 is an isometric view of a device that incorporates the present invention.

FIG. 2 is a cross section of a side view illustrating the present invention in a first inflating position.

DETAILED DESCRIPTION OF THE PREFERRED EMBODIMENT

Figure 3:
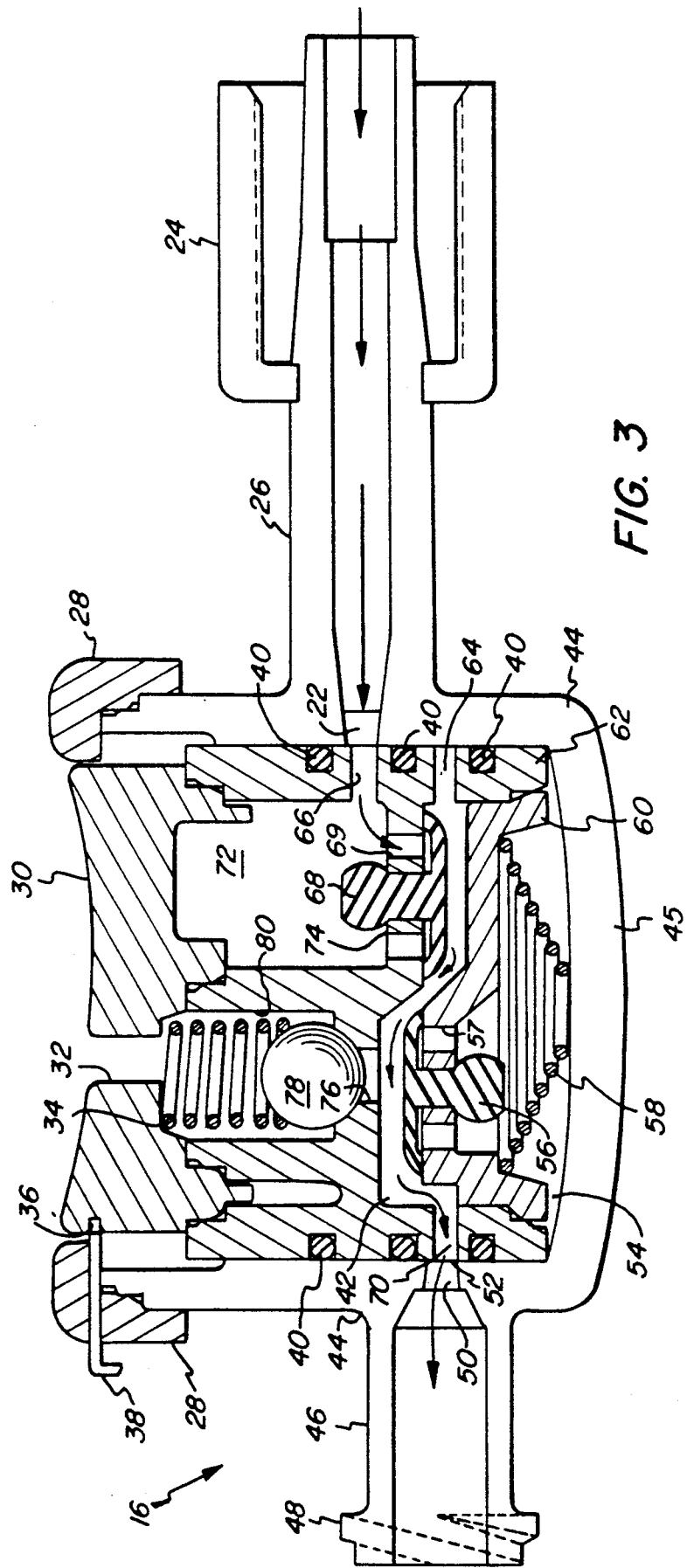
FIG. 3 is a cross section of a side view of the present invention in a second deflating position.

FIG. 1 illustrates a vascular dilating device that incorporates the present invention. Handle 10 provides a mechanical advantage to force plunger 12 into cylinder 14. A fluid in cylinder 14 is forced through valve 16. A pressure gauge 18 gives an accurate reading of the fluid pressure. The pressure is thereby built up in balloon catheter 20. Prior to being inflated with fluid, the balloon catheter 20 is positioned appropriately in an artery that is to be worked upon. After being inserted, the balloon catheter 20 is inflated by squeezing handle 10 to develop fluid pressure therein. While pressure is being developed, pressure gauge 18 is closely watched. Depending upon various pressure readings, patient history, and other factors, the physician determines precisely how much pressure to develop in the balloon catheter 20, as well as at what point to release the pressure. Under some circumstances, the release of pressure needs to be accomplished very quickly. The speed at which the pressure is released can, in some circumstances, be very critical. This is especially true should a complication arise where the artery being worked upon nears rupture. Valve 16 permits rapid release of pressure within the balloon catheter, thereby deflating it.

FIG. 2 better illustrates the structure and function of the improved valve of the present invention. FIG. 2 illustrates valve 16 in a first inflating position. The balloon catheter 20 is attached to the valve by catheter tube 26 and coupling 24. The catheter tube 26 is attached to a cup shaped body 44. An aperture 22 leads from the catheter tube 26 into the cup shaped body 44. At the other end of the cup shaped body 44 is a tube 46. Tube 46 attaches to cylinder 14, illustrated in FIG. 1, by collar 48. Tube 46 is attached to the body 44. An aperture 50 leads into the body 44 from the tube 46. A piston 62 is adapted to slide within the body 44. The piston 62 has a plurality of chambers and openings therein. Along the perimeter wall of the cylinder 62 is a pressure release inlet opening 66, a passage outlet opening 64, an inlet chamber opening 52 and a pressure release outlet opening 70. Opening 66 opens into a pressure release chamber 72. Opening 52 enters into an inlet chamber 54. Between opening 64 and opening 70 is a passage 42.

A bottom plate 60 is attached to the piston 62. Bottom plate 60 forms a portion of the surface defining the passage 42. A spring 58 is located between the bottom plate 60 and the bottom portion 45 of body 44. The other surface of passage 42 is formed by top plate 74. Piston 62 is retained in the body 44 by cap 28. The top portion of piston 62 is covered by button 30. Through button 30 is a relief opening 32. Relief opening 32 enters into a relief chamber 80. A relief ball 78 at the bottom of the relief chamber 80 seals a relief aperture 76. A relief spring 34 retains ball 78 in aperture 76. Aperture 76 enters into passage 42.

Between chamber 54 and passage 42 is an inlet valve opening 57. Placed within opening 57 is a one-way inlet valve 56. Valve 56 permits fluid to flow in one direction only from chamber 54 into passage 42. Between chamber 72 and passage 42 is an outlet valve opening 69. Within opening 69 is positioned a one-way outlet valve 68. Valve 68 permits fluid to flow in one direction only from chamber 72 into passage 42.

Spring 58 normally biases piston 62 upward into a first inflating position. Button 30, when depressed downward, forces piston 62 into a second deflating position. Piston 62 can be maintained in this second position by a latch 38 passing through cap 28 being slid into notch 36 in button 30. The hold down latch 38 while helpful in some applications need not be used or even included in others. Because piston 62 moves within body 44, seals 40 are used to prevent any leakage therebetween.

If during inflation the pressure exceeds a predetermined safety limit, a relief valve is provided. Should the pressure exceed the predetermined limit, fluid is forced through aperture 76, past ball 78 and out opening 32. The spring 34 is selected to provide a force sufficient to prevent fluid leakage until the predetermined pressure is obtained.

FIG. 3 illustrates the present invention in a second deflating position. In this position, the pressurized fluid within the balloon catheter 20 is permitted to flow through valve 16, resulting in the balloon catheter deflating. As is illustrated in FIG. 3, when button 30 is depressed, piston 62 is forced into a second position. In this second position, opening 66 aligns with aperture 22 and opening 70 aligns with aperture 50. This establishes a path through which the pressurized fluid in the balloon catheter 20 can escape.

The operation of the present invention can readily be understood with reference to FIGS. 1-3. In FIG. 2, when the valve 16 is in a first inflating position, fluid can enter tube 16 from the syringe illustrated generally by plunger 12 and cylinder 14 in FIG. 1. The fluid enters aperture 50 and enters into the inlet chamber 54. The pressurized fluid, once in chamber 54, flows through opening 57 and one-way inlet valve 56 into the passage 42. Once in passage 42, the pressurized fluid is free to flow through opening 64 and aperture 22 into tube 26. Tube 26 is coupled to the balloon catheter 20. Therefore, when the valve 16 is in this first position, the pressure generated by the handle portion of the device illustrated in FIG. 1 is readily transmitted to the balloon catheter.

The balloon catheter can quickly be deflated by simply pressing button 30 on valve 16. Upon pressing button 30 piston 62 is depressed into a second deflating position. This second position is illustrated in FIG. 3. With reference to FIG. 3, pressurized fluid can flow from the balloon catheter 20 into tube 26 and through aperture 22 in body 44. From aperture 22, fluid is permitted to flow through opening 66 and into chamber 72. From chamber 72, fluid can flow through opening 69 and one-way valve 68 into passage 42. From passage 42, the fluid can exit through opening 70 and aperture 50 into tube 46. A negative pressure can be developed in tube 46 by withdrawing plunger 12 from cylinder 40 illustrated in FIG. 1, to assist deflation of the balloon catheter 20.

From the detailed description of the present invention, it can readily be appreciated that the present invention permits a physician to rapidly and easily deflate a balloon catheter should it become necessary during an angioplasty procedure. The deflation can also be accomplished without the physician having to remove his hand from the device, thereby maintaining better control of the device during the critical period when deflation needs to be performed quickly.

Although the preferred embodiment has been illustrated and described, it will be obvious to those skilled in the art that various modifications may be made without departing from the spirit and scope of this invention.

What is claimed is:

1. An improved valve for use in a vascular dilating device for performing a coronary angioplasty procedure comprising:

a cup shaped body having a first and second aperture therein;

a piston, adapted to slide within said body and capable of being placed into a first and second position, having a plurality of chambers therein, a plurality of openings in the perimeter of the piston wall adjacent said body, and a passage extending substantially transversely from one end to the other;

biasing means, placed within said body, for biasing said piston upward into said first position forming an inlet chamber between the bottom of said piston and the bottom of said body;

one of said plurality of openings being on inlet chamber opening, said inlet chamber opening permitting flow between said first aperture and said inlet chamber when said piston is in said first position; and a one way inlet valve permitting fluid to enter said passage from said inlet chamber;

one of said plurality of openings being a passage outlet opening, said passage outlet opening permitting flow between said passage and said second aperture when said piston is in said first position;

one of said plurality of chambers being a pressure release chamber;

one of said plurality of openings being a pressure release inlet opening permitting flow between said second aperture and said pressure release chamber when said piston is in said second position;

a one way outlet valve permitting fluid to enter said passage from said pressure release chamber;

one of said plurality of openings being a pressure release outlet opening, said pressure release outlet opening permitting flow between said passage and said first aperture when said piston is in said second position.

2. An improved valve for use in a vascular dilating device for performing a coronary angioplasty procedure as in claim 1 further comprising:

safety relief means, associated with said passage, for relieving pressure within the passage when the pressure exceeds a predetermined safety limit.

3. An improved valve for use in a vascular dilating device for performing a coronary angioplasty procedure as in claim 2 wherein said safety relief means comprises:

said passage having a relief aperture therein;
a ball; and
a spring forcing said ball adjacent said relief aperture preventing fluid from flowing through said aperture until a predetermined fluid pressure safety limit is reached.

4. An improved valve for use in a vascular dilating device for performing a coronary angioplasty procedure as in claim 1 further comprising:

seal means, placed between said body and said piston, for preventing leakage from said plurality of openings.

5. An improved valve for use in a vascular dilating device for performing a coronary angioplasty procedure as in claim 1 further comprising:

cap means, positioned on the open end of said body, for retaining said pisiton within said body; and
a button attached to the end of said piston adjacent said cap means.

6. An improved valve for use in a vascular dilating device for performing a coronary angioplasty procedure as in claim 5 further comprising:

latch means, associated with said button, for holding said piston in said second position until released.

* * * * *